United States Patent [19]

Aumueller et al.

[11] Patent Number: 5,008,312
[45] Date of Patent: Apr. 16, 1991

[54] 2,6-POLYALKYLPIPERIDINE-SUBSTITUTED BISLACTAMS AND THEIR USE FOR THE STABILIZATION OF ORGANIC MATERIAL, IN PARTICULAR OF PLASTICS, AND MATERIALS STABILIZED THEREWITH

[75] Inventors: Alexander Aumueller, Deidesheim; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 390,216

[22] Filed: Aug. 7, 1989

[30] Foreign Application Priority Data

Aug. 16, 1988 [DE] Fed. Rep. of Germany ....... 3827641

[51] Int. Cl.$^5$ ................. C08K 5/3417; C07D 401/00
[52] U.S. Cl. ..................... 524/92; 546/187; 524/100; 524/120; 524/128; 524/153; 524/291; 524/302; 524/304; 524/342; 524/403
[58] Field of Search ................. 529/92; 546/187; 524/100, 120, 128, 153, 291, 302, 304, 342, 403

[56] References Cited

U.S. PATENT DOCUMENTS 3,684,765 8/1972 Matsui et al. .............. 524/102
4,659,775 4/1987 Pfenninger et al. ............ 524/92

FOREIGN PATENT DOCUMENTS 2040975 2/1972 Fed. Rep. of Germany .

Primary Examiner—Kriellion Morgan
Attorney, Agent, or Firm—Oblon, Spivak, McClelland, Maier & Neustadt

[57] ABSTRACT

Bislactams of the general formula I

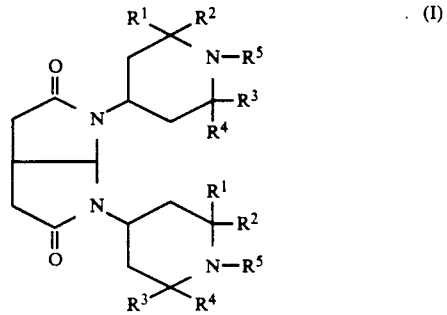

where $R^1$, $R^2$, $R^3$ and $R^4$ independently of one another are each $C_1$-$C_4$-alkyl, or $R^1$ and $R^2$ and/or $R^3$ and $R^4$ form a tetra- or pentamethylene radical, and $R^5$ is hydrogen, carbonyl-$C_1$-$C_8$-alkyl, benzoyl, $C_1$-$C_8$-alkyl, $C_7$-$C_{10}$-phenylalkyl, the phenyl nucleus being unsubstituted or substituted by one or two $C_1$-$C_4$-alkyl, $C_1$-$C_4$-alkyoxy, fluorine, chlorine or bromine radicals, or is $C_1$-$C_3$-cyanoalkyl, $C_2$-$C_4$-hydroxyalkyl or $C_2$- or $C_3$-aminoalkyl, and the acid addition salts and hydrates of these compounds.

The compounds (I) are stabilizers for organic materials.

13 Claims, No Drawings

2,6-POLYALKYLPIPERIDINE-SUBSTITUTED BISLACTAMS AND THEIR USE FOR THE STABILIZATION OF ORGANIC MATERIAL, IN PARTICULAR OF PLASTICS, AND MATERIALS STABILIZED THEREWITH

It is known that polyalkylpiperidine derivatives protect organic polymers from destruction by light and heat.

Unsatisfactory properties of the prior art compounds are frequently the poor compatibility with polyolefins and/or other plastics, the duration of the protective action, the natural color of the substances, the tendency to volatility and the thermal decomposition of the stabilizers during incorporation in the polymer at elevated temperatures.

It is an object of the present invention to provide novel stabilizers which do not have the above disadvantages.

We have found that this object is achieved with the aid of bislactams of the invention. The present invention accordingly relates to bislactams of the general formula I

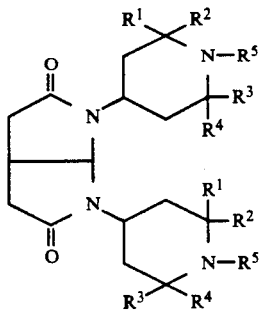

(I)

where $R^1$, $R^2$, $R^3$ and $R^4$ independently of one another are each $C_1-C_4$-alkyl, or $R^1$ and $R^2$ and/or $R^3$ and $R^4$ together form a tetra- or pentamethylene radical, and $R^5$ is hydrogen, carbonyl-$C_1-C_8$-alkyl, benzoyl, $C_1-C_8$-alkyl, $C_7-C_{10}$-phenylalkyl, the phenyl nucleus being unsubstituted or substituted by one or two $C_1-C_4$-alkyl, $C_1-C_4$-alkoxy, fluorine, chlorine or bromine radicals, or is $C_1-C_3$-cyanoalkyl, $C_2-C_4$-hydroxyalkyl or $C_2$-or $C_3$-aminoalkyl, and the acid addition salts and hydrates of these compounds.

Because of their good compatibility with organic materials, especially in plastics and surface coating binders, the compounds (I) are very suitable as stabilizers for these materials. The colorless compounds are nonvolatile and sufficiently stable to permit them to be incorporated into plastics at elevated temperatures.

The novel compounds are particularly suitable for the stabilization of polyolefins, in particular of ethylene polymers and propylene polymers, of polyurethanes and coatings.

Alkyl groups $R^1$, $R^2$, $R^3$ and $R^4$ are, for example, methyl, ethyl, n-propyl, isopropyl, n-butyl or isobutyl. Two adjacent radicals $R^1$ and $R^2$ and/or $R^3$ and $R^4$ may together furthermore form a tetra- or pentamethylene radical.

$R^1$, $R^2$, $R^3$ and $R^4$ are each preferably methyl.

Alkyl radicals $R^5$ may be linear or branched. Specific examples are methyl, ethyl, propyl, n-butyl, n-pentyl, isopentyl, n-hexyl, n-heptyl and n-octyl. The preferred alkyl radical $R^5$ is methyl.

Carbonylalkyl radicals $R^5$ are, for example, propionyl, butanoyl, pentanoyl, hexanoyl, heptanoyl and octanoyl, as well as benzoyl and in particular acetyl. Phenylalkyl radicals $R^5$ are, for example, phenylethyl and preferably benzyl.

Examples of phenylalkyl radicals $R^5$ which are substituted in the phenyl nucleus are 3- and 4-methoxybenzyl, 3- and 4-methoxyphenylethyl, 3- and 4-chlorobenzyl, 3- and 4-chlorophenylethyl, 3- and 4-ethoxybenzyl, 3- and 4-ethoxyphenylethyl and 3- and 4-methylbenzyl, of which 3- and 4-methylbenzyl are preferred. Cyanoalkyl radicals $R^5$ are, for example, cyanoethyl and preferably cyanomethyl.

Examples of suitable hydroxyalkyl and aminoalkyl radicals $R^5$ are 3-hydroxypropyl, 4-hydroxybutyl, 2-hydroxyethyl, 3-aminopropyl and 2-aminoethyl. Among these, 2-hydroxyethyl and 2-aminoethyl are preferred. $R^5$ is particularly preferably hydrogen.

The compounds (I) can be prepared similarly to the method described in DE-A 2 325 429, by aminolysis of the compound of the formula (II) with an amine of the general formula (III) in the presence or absence of a solvent and in the presence or absence of a catalyst. Preferably, the process is carried out using an excess of amine in the absence of a solvent and catalyst, at from 100° to 220° C., preferably from 120° to 150° C.

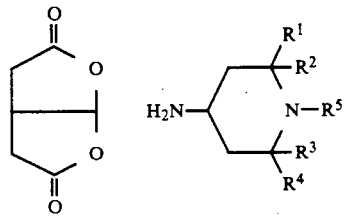

(II)          (III)

Compounds of the general formula (I) where $R^5$ is hydrogen can be converted into compounds of the general formula (I) where $R^5$ is not hydrogen by processes known from the literature, such as alkylation, acylation, a Michael addition reaction, cyanomethylation or hydroxyalkylation.

The novel compounds (I) may be in the form of the free bases or in the form of hydrates or salts. Suitable anions are derived from, for example, inorganic acids, carboxylic acids and sulfonic acids. Among the salts, those of the carboxylic acids and sulfonic acids are preferred.

Examples of suitable inorganic anions are chloride, bromide, sulfate, methosulfate, tetrafluoroborate, phosphate and thiocyanate.

Examples of carboxylate anions are formate, acetate, propionate, hexanoate, cyclohexanoate, lactate, stearate, palmitate, dodecylbenzoate, benzoate, acrylate, methacrylate, citrate, malonate and succinate, and anions of polycarboxylic acids, such as polyacrylic acid and polymethacrylic acid, and of copolymers containing (meth)acrylic acid and having up to 3000 COOH groups.

Examples of sulfonate anions are benzenesulfonate, tosylate and methylsulfonate.

The compounds (I) are added in a concentration of from 0.01 to 5, preferably from 0.02 to 2, % by weight to the plastics to be stabilized, before, during or after polymer formation.

For the preparation of the mixtures from the novel compounds and the plastics to be stabilized, all known processes for mixing stabilizers or other additives into polymers can be used.

In addition to the novel compounds (I), the stabilized plastics may also contain further additives, for example antioxidants, additional light stabilizers, metal deactivators, antistatic agents and flame retardant agents, as well as pigments and fillers.

Antioxidants and light stabilizers which can be added to the plastics in addition to the novel compounds are, for example, compounds based on sterically hindered phenols and costabilizers containing sulfur and/or phosphorus.

Examples of such phenolic antioxidants are 2,6-di-tert-butyl-4-methylphenol, n-octadecyl β-(3,5-di-tert-butyl-4-hydroxyphenyl)-propionate, 1,1,3-tris-(2-methyl-4-hydroxy-5-tert-butylphenyl)-butane, 1,3,5-trimethyl-2,4,6-tris-(3,5-di-tert-butyl-4hydroxybenzyl)-benzene, 1,3,5-tris-(3,5-di-tert-butyl-4-hydroxybenzyl) isocyanurate, 1,3,5-tris-[β-(3,5-di-tert-butyl-4-hydroxyphenyl)-propionyloxyethyl] isocyanurate, 1,3,5-tris-(2,6-dimethyl-3-hydroxy-4-tert-butylbenzyl) isocyanurate and pentaerythritol tetrakis-[β-(3,5-di-tert-butyl-4-hydroxyphenyl)-propionate].

Examples of suitable phosphorus-containing antioxidants are tris-(nonylphenyl) phosphite, distearyl pentaerythritol diphosphite, tris-(2,4-di-tert-butylphenyl) phosphite, tris-(2-tert-butyl-4-methylphenyl) phosphite, bis-(2,4-di-tert-butylphenyl) pentaerythritol diphosphite and tetrakis-(2,4-di-tert-butylphenyl)-4,4'-biphenylene diphosphite.

Examples of sulfur-containing antioxidants are dilauryl thiodipropionate, dimyristyl thiodipropionate, distearyl thiodipropionate, pentaerythritol tetrakis-(β-laurylthiopropionate) and pentaerythritol tetrakis-(β-hexylthiopropionate).

Further antioxidants and light stabilizers which may be used together with the novel compounds are, for example, 2-(2'-hydroxyphenyl)-benzotriazoles, 2-hydroxybenzophenones, phenyl esters of hydroxybenzoic acids, α-cyanocinnamic acid derivatives, nickel compounds, benzimidazolcarboxanilides and/or oxalic acid dianilides.

Examples of suitable organic polymers which can be stabilized by the novel compounds are:

polymers of mono- and diolefins, such as low and high density polyethylene, linear low density polyethylene, polypropylene, polyisobutylene, polybut-1-ene, polyisoprene, polybutadiene and copolymers of mono- and diolefins and blends of the stated polymers;

copolymers of mono- or diolefins with other vinyl monomers, for example ethylene/alkyl acrylate copolymers, ethylene/alkyl methacrylate copolymers, ethylene/vinyl acetate copolymers or ethylene/acrylic acid copolymers; polystyrene;

copolymers of styrene or α-methylstyrene with dienes or acrylyl derivatives, such as styrene/butadiene, styrene-acrylonitrile, stryene/ethyl methacrylate, styrene-butadiene/ethyl acrylate or styrene/acrylonitrile/-methacrylate;

ABS, MBS or similar polymers;

halogen-containing polymers, e.g. polyvinyl chloride, polyvinyl fluoride, polyvinylidene fluoride and their copolymers;

polymers derived from α,β-unsaturated acids and their derivatives, such as polyacrylates and polymethacrylates, polyacrylamides and polyacrylonitriles; polymers derived from unsaturated alcohols and amines or their acrylyl derivatives or acetals, such as polyvinyl alcohol or polyvinyl acetate;

polyurethanes, polyamides, polyureas, polyesters, polycarbonates, polysulfones, polyether sulfones and polyether ketones.

Further organic polymers which can be stabilized with the novel compounds are surface coatings, of which the baking finishes are particularly noteworthy, and among these in turn automative finishes, preferably two-coat systems, are particularly noteworthy. In this case too, the abovementioned further antioxidants and light stabilizers can also be added.

The novel compounds can be added to the coating in solid or dissolved form. The good solubility of (I) in the coating systems is particularly advantageous in this respect.

EXAMPLE 10 g of 2,8-dioxa-cis-bicyclo[3.3.0]octa-3,7-dione (preparation: Tetrahedron 36 (1980), 321) in 80 ml of 4-amino-2,2,6,6-tetramethylpiperidine were heated for 3 hours at 120° C. and then for 5.5 hours at 150° C. After the mixture had cooled, 250 ml of petroleum ether were added, the precipitate which had separated out was filtered off under suction, washed with petroleum ether and extracted by boiling with ethanol, and the product was filtered off under suction while hot. 24.0 g of the compound of the formula

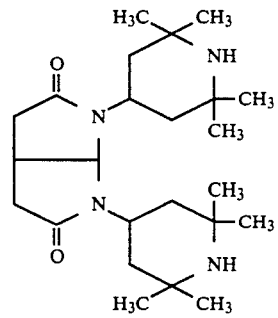

were obtained as a colorless solid of melting point 257° C. The compound crystallized with one mole of water of crystallization.

Calculated: C 66.0; H 10.2; N 12.8; O 11.0;
Found: C 65.9; H 10.1; N 12.6; O 11.4.

We claim:

1. A bislactam of the formula I

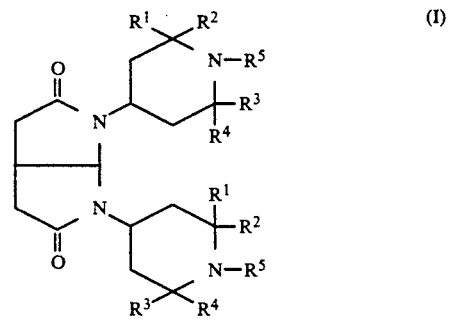

where $R^1$, $R^2$, $R^3$ and $R^4$ independently of one another are each $C_1$-$C_4$-alkyl, or $R^1$ and $R^2$ or $R^3$ and $R^4$ or $R^1$ and $R^2$ and $R^3$ and $R^4$ form a tetra- or pentamethylene radical, and $R^5$ is hydrogen, carbonyl-$C_1$-$C_8$-alkyl, benzoyl, $C_1$-$C_8$-alkyl, $C_7$-$C_{10}$-phenylalkyl, the phenyl nucleus being unsubstituted or substituted by one or two $C_1$-$C_4$-alkyl, $C_1$-$C_4$-alkoxy, fluorine, chlorine or bromine radicals, or is $C_1$-$C_3$-cyanoalkyl, $C_2$-$C_4$-hydroxyalkyl, $C_2$- or $C_3$-aminoalkyl, and the acid addition salts and hydrates of these compounds.

2. A bislactam as claimed in claim 1, wherein $R^1$, $R^2$, $R^3$ and $R^4$ are each methyl.

3. A bislactam as claimed in claim 1, wherein $R^5$ is hydrogen, methyl, acetyl, benzyl, 3-methylbenzyl, 4-methylbenzyl, cyanomethyl, 2-hydroxyethyl or 2-aminoethyl.

4. A bislactam as claimed in claim 2, wherein $R^5$ is hydrogen, methyl, acetyl, benzyl, 3-methylbenzyl, 4-methylbenzyl, cyanomethyl, 2-hydroxyethyl or 2-aminoethyl.

5. A bislactam as claimed in claim 1, wherein $R^5$ is hydrogen.

6. A bislactam as claimed in claim 2, wherein $R^5$ is hydrogen.

7. A stabilized synthetic resin containing one or more lactams as claimed in claim 1.

8. A stabilized synthetic resin as claimed in claim 7, wherein said stabilized synthetic resin comprises a plastic.

9. A stabilized synthetic resin as claimed in claim 7, wherein said stabilized synthetic resin comprises a surface coating.

10. A stabilized synthetic resin as claimed in claim 7, wherein said stabilized synthetic resin comprises at least one polyolefin.

11. A stabilized synthetic resin as claimed in claim 7, wherein said stabilized synthetic resin is selected from the group consisting of polyurethanes, polyamides, polyureas, polyesters, polycarbonates, polysulfones, polyether sulfones and polyether ketones.

12. A plastic as claimed in claim 8, further comprising at least one additive selected from the group consisting of anti-oxidants, additional light stabilizers, metal deactivators, anti-static agents, flame-retardant agents, pigments and fillers.

13. A surface coating as claimed in claim 9, wherein said surface coating is a two-coat automotive finish.

* * * * *